(12) United States Patent
Sawyer

(10) Patent No.: US 10,307,546 B2
(45) Date of Patent: Jun. 4, 2019

(54) REUSABLE SYRINGE ASSEMBLY INCLUDING RETRACTABLE PROTECTIVE SHIELDING FRAME

(71) Applicant: Ultimate Syringetek Inc., Vancouver (CA)

(72) Inventor: Melvyn Lloyd Sawyer, Vancouver (CA)

(73) Assignee: ULTIMATE SYRINGETEK INC., Vancouver, BC (CA)

( * ) Notice: Subject to any disclaimer, the term of this patent is extended or adjusted under 35 U.S.C. 154(b) by 51 days.

(21) Appl. No.: 15/452,657

(22) Filed: Mar. 7, 2017

(65) Prior Publication Data

US 2017/0312452 A1 Nov. 2, 2017

Related U.S. Application Data

(60) Provisional application No. 62/331,073, filed on May 3, 2016, provisional application No. 62/328,860, filed on Apr. 28, 2016.

(51) Int. Cl.
    *A61M 5/28* (2006.01)
    *A61M 5/31* (2006.01)
    *A61M 5/32* (2006.01)

(52) U.S. Cl.
    CPC ............ *A61M 5/3245* (2013.01); *A61M 5/28* (2013.01); *A61M 5/3137* (2013.01);
    (Continued)

(58) Field of Classification Search
    CPC .... A61M 5/3245; A61M 5/3137; A61M 5/28; A61M 2207/00; A61M 2205/02; A61M 2005/3142
    See application file for complete search history.

(56) References Cited

U.S. PATENT DOCUMENTS 3,848,593 A * 11/1974 Baldwin ................ A61M 5/24
                                                     604/206
4,723,943 A *  2/1988 Spencer ............ A61M 5/3271
                                                       5/947

(Continued)

OTHER PUBLICATIONS

Canadian Intellectual Property Office as the International Preliminary Examining Authority, International Preliminary Report on Patentability dated Jul. 25, 2018 (PCT/CA2017/050516).

(Continued)

*Primary Examiner* — Lauren P Farrar
(74) *Attorney, Agent, or Firm* — Kevin R. Erdman; Brannon Sowers & Cracraft PC

(57) ABSTRACT

The present invention involves a sterilizable syringe allows for reduction in needlestick injuries using conventional sterile needles. The syringe allows for direct access to and the safe removal and disposal of needles. The device consists of a sterilizable, reusable hypodermic syringe to which a disposable needle is attached, and employs carpules containing injectable medication, viewable and either manually or automatically aspirating. Some embodiments have a protective sliding mechanism consisting of an open frame bearing one or more protective collars, one at the furthermost end of the frame and an optional second one at a more proximal position. The protective mechanism may be extended to protect an exposed needle tip and retracted during an injection. With the protective mechanism extended, the needle mounting hub is exposed to allow for its exchange or removal and safe disposal. The protective mechanism is engaged until immediately prior to the delivery of medication, disengaged on delivery, and engaged after delivery.

39 Claims, 4 Drawing Sheets

(52) U.S. Cl.
CPC . *A61M 2005/3142* (2013.01); *A61M 2205/02* (2013.01); *A61M 2207/00* (2013.01)

(56) References Cited

U.S. PATENT DOCUMENTS

| | | | |
|---|---|---|---|
| 6,719,736 B2 | 4/2004 | Collins et al. | |
| 8,211,065 B2* | 7/2012 | Miller | A61M 5/3257 604/198 |
| 8,372,044 B2 | 2/2013 | Westbye et al. | |
| 2002/0147430 A1* | 10/2002 | Collins | A61M 5/3243 604/218 |
| 2012/0046615 A1* | 2/2012 | Koiwai | A61M 5/3243 604/192 |
| 2015/0126939 A1* | 5/2015 | Quinn | A61M 5/3271 604/198 |

OTHER PUBLICATIONS

Canadian Intellectual Property Office as the International Searching Authority, International Search Report dated Aug. 2, 2017 (PCT/CA2017/050516).

Canadian Intellectual Property Office as the International Searching Authority, Written Opinion of the International Searching Authority dated Aug. 2, 2017 (PCT/CA2017/050516).

\* cited by examiner

REUSABLE SYRINGE ASSEMBLY INCLUDING RETRACTABLE PROTECTIVE SHIELDING FRAME

CROSS-REFERENCE TO RELATED APPLICATIONS

The present application claims priority under 35 U.S.C. § 119(e) of U.S. Provisional Patent Application Ser. No. 62/328,860 filed Apr. 28, 2016 and Ser. No. 62/331,073 filed May 3, 2016, the disclosures of which are incorporated in full herein.

BACKGROUND OF THE INVENTION

Field of the Invention

The present invention relates to a syringe assembly comprising a reusable housing that accommodates disposable, pre-proportioned anesthetic cartridge ampoules, or carpules, therein and disposable needles, and more particularly the present invention relates to a syringe assembly supporting a protective shielding frame thereon which is slidable between an extended position shielding the needle tip and a retracted position in which the needle is unobstructed for administering the anesthetic to a patient.

Description of the Related Art

Percutaneous injuries (sharp object punctures through the skin) pose a risk of transmission of blood borne pathogens to healthcare workers. Needle stick injuries are a large component of such percutaneous injuries. Accidental contact and injury with contaminated hollow bore needles may expose a health care worker to blood borne diseases including the Hepatitis B virus and HIV. A significant number of such percutaneous needle stick injuries occur immediately prior to or after injection, or due to mishandling and improper disposal of these sharps. Many of these injuries to healthcare providers could be preventable.

As a strategic method of risk reduction to all health care workers, regulatory bodies in the US, Canada and elsewhere have established guidelines, regulations and standards aimed at reducing needle stick injuries. The use of safety engineered syringes, i.e. syringes that are designed to prevent or reduce these types of injuries have been mandated. Medical use of needle/syringe apparatuses includes those syringes employing hollow bore needles that are placed intra-vascularly to withdraw blood or to inject a liquid into the bloodstream, and those syringes using needles which withdraw a liquid from a small container into a reservoir in the syringe. Then, the contents of the syringe are delivered either intra-vascularly or interstitially. These syringes as well as the needles are single use and disposable.

While safety engineered syringes that have self-retracting needles after use are now commonly used in medicine, the application and use of these types of syringes in, for example, dental use has generally not been successful, due to the differing nature in the use of syringes. Generally, syringes with needles in dentistry are used to deliver one or multiple doses of local anesthetic using needles of differing lengths and sharpness. Local anesthetic is administered via these reusable, sterilizable syringes using disposable, pre-proportioned anesthetic cartridge carpules and delivered using single patient use, sheathed sterile narrow bore needles attached to the syringe. These conventional needles are available pre-packaged, sterile, with protective sheaths on either end that are removed during use. The short distal end of the needle is attached to the syringe by the needle mounting hub after removal of the sheath covering the distal end, and the longer delivery end of the needle is to remain covered by its sheath until use. This latter sheath is then manually replaced after use and prior to disposal of the needle apparatus. A needle of one size and/or bore may be replaced during a patient care visit with a needle of another size/bore after disposal of the first needle used. It is sometimes necessary to use multiple cartridge carpules during a patient care visit, and needles must be resheathed prior to replacing spent carpules. The act of re-sheathing and disposing of these exposed needles bring a high risk of accidental needle stick injuries to the operator or assistant, which is a great concern in the transmission of blood borne diseases.

There must be an aspirating feature to all dental anesthetic syringes to preclude accidental delivery of local anesthetic intra-vascularly. 'Aspiration' is the small withdrawal of local anesthetic on injection using either a reverse pulling motion of the syringe plunger as it is engaged with the carpule (harpoon method), or on release of the plunger thus releasing pressure of the top end of the carpule, acting as a gasket, on the body of the syringe (self-aspirating method). If blood is visible when using this technique, injection into a blood vessel has occurred. The operator must immediately cease injecting, withdraw the needle and move to another injection site. A clear view of the aspirant is necessary.

Local anesthetic is delivered using one or multiple carpules, sometimes over the time of a particular dental procedure. The need to remove and replace the protective needle sheath when the syringe is not in use places the dental healthcare worker at risk for a needle stick injury. Also, improper handling and disposal of the needle when exchanging needles during a procedure or at the end of the procedure may lead to accidental needle punctures. However, not all needle stick injuries may be preventable. Non-preventable injuries occur due to unexpected patient movement immediately prior to, during or immediately after the delivery of local anesthetic when the needle is unsheathed, or through self-inflicted accidental operator injuries. Preventable injuries are those that occur during the recapping of exposed needles or on their disposal. This invention relates to a sterilizable local anesthetic syringe with a needle protection mechanism, the use of which may reduce the risk of accidental needle stick injuries, whether they be preventable or non-preventable.

Designing a safety syringe, using pre-apportioned carpules and/or multiple needles that will allow for multiple injections over a period of time of the procedure, as is commonplace in for example, dentistry, has presented challenges. This is due in part because most prior iterations of a dental safety syringe have been based on the medical model, which employs single use disposable syringes or needle apparatuses. Having a retractable needle with a requirement for that needle to be able to be reactivated or changed in the course of delivering multiple injections over a time period has confounded inventors. Also, current designs of so-called safe syringes use plastic barrel covers that may impede vision of aspirant when the cover is retruded during the delivery, and aspiration, of local anesthetic.

Various examples of prior art syringes are described in the following United States Patents: U.S. Pat. No. 3,583,399 by Ritsky; U.S. Pat. No. 3,618,603 by Levenson; U.S. Pat. No. 4,333,456 by Webb; U.S. Pat. No. 4,333,457 by Margulies; U.S. Pat. No. 4,540,405 by Miller et al; U.S. Pat. No. 4,747,837 by Hauck; U.S. Pat. No. 4,772,272 by McFarland;

U.S. Pat. No. 5,045,066 by Scheuble et al; U.S. Pat. No. 5,053,018 by Talonn et al; U.S. Pat. No. 5,336,185 by Lynch et al; U.S. Pat. No. 5,437,647 by Firth et al; U.S. Pat. No. 5,876,379 by Beauvais et al; U.S. Pat. No. 6,416,323 by Grenfell et al; U.S. Pat. No. 6,719,736 by Collins et al; U.S. Pat. No. 7,850,646 by Segal; and U.S. Pat. No. 8,029,279 by Dillard.

The prior art describes various iterations of self-aspirating dental anesthetic syringes with no associated needle stick risk-reducing safety features. Where safety features have been introduced, plastic protective sheaths have been employed and housed on the needle apparatus. In some cases, there are single use carpule—needle apparatuses with sliding circular plastic sheaths and reusable plungers. Some designs describe a spring loaded sheath which is retracted in a locked position during injection and then disengaged so that it returns to a covering position over the exposed needle post injection. In prior art, systems are described which use a retractable disposable shield which covers an exposed needle. These systems typically do not allow for the use of commonly available disposable needles and do not allow for the replacement or exchange of needles on the same apparatus during treatment of a single patient. As they are not intended for re-use, and also due to the plastics used, they may be unstable upon use and create an environmental burden on disposal. Another system described by Segal includes a prescribed needle disposal device. Dentists, for example, have typically used the self-aspirating type syringes originally described by Ritsky, and are accustomed to their sturdiness, reliability, ease of use and 'sterilizability'.

SUMMARY OF THE INVENTION

In a first aspect a reusable syringe assembly is provided for use with a disposable carpule containing a liquid and a disposable needle having a needle tip, the assembly comprising: a syringe housing extending longitudinally between a first housing end and a second housing end, the housing adapted to receive thereon the disposable needle and defining a receptacle arranged to receive therein the carpule such that the carpule is in fluid communication with the disposable needle tip; and a protective shielding frame supported on the housing for longitudinal sliding between a first extended position in which the protective shielding frame protrudes longitudinally beyond the second housing end to surround the needle tip of the disposable needle and a second retracted position in which the protective shielding frame is retracted towards the first housing end relative to the extended position; wherein the protective shielding frame is arranged to provide manual access through an aperture in the protective shielding frame to the needle mounting hub when the protective shielding frame is in the extended position.

The protective shielding frame may be arranged to render the disposable carpule visible through the protective shielding frame when the protective shielding frame is in the retracted position. The housing may include along one side thereof an access opening suitably sized to permit the carpule to be inserted into and removed from the housing therethrough, the protective shielding frame being supported on the housing such that the access opening is unobstructed by the protective shielding frame when the protective shielding frame is in at least the extended position of the protective shielding frame. The protective shielding frame may be arranged to render the disposable carpule visible, and in some embodiments directly visible, through the protective shielding frame when the protective shielding frame is in the retracted position. The protective shielding frame may comprise at least one longitudinal frame member and at least one collar portion fixed to the longitudinal frame member so as to surround the tip of the disposable needle. The at least one collar portion may comprise two collar portions at longitudinally spaced positions. The assembly may further comprise a plunger arranged to operatively engage the carpule and supported for longitudinal sliding movement relative to the first end of the housing. The plunger may include a finger grip portion and an eyelet. The reusable syringe assembly is sterilizable and may be made in its entirety from one or more dimensionally stable sterilizable medical grade materials. More specifically, it may be made in its entirety from at least one of medical grade stainless steel and chrome plated brass. In some embodiments, reusable syringe assembly may be made in its entirety from one or more autoclavable polymers.

One goal of this invention is to provide a stable, reusable device with a novel safety feature that reduces the risk of accidental needle stick injury during an injection procedure and enables the use and safe disposal of the currently commercially available array of disposable needles.

In a further aspect a method is provided of operating a syringe assembly according to the above description having a disposable carpule received therein and a disposable needle coupled to the second end of the housing, the method comprising visually inspecting the carpule for aspirant through the protective shielding frame when the protective shielding frame is in the retracted position.

In a further aspect a reusable syringe assembly is provided for use with a disposable needle and a disposable carpule, the assembly comprising: a housing extending longitudinally between a first end and a second end comprising a needle mounting hub adapted to support the disposable needle thereon and defining a receptacle therein, the receptacle arranged to receive therein the carpule such that the carpule is cooperative with the disposable needle; a plunger supported for sliding movement relative to the first end of the housing so as to be arranged to operatively engage the carpule; and a protective shielding frame supported on the housing for longitudinal sliding between an extended position in which the protective shielding frame protrudes longitudinally beyond the second end of the housing and surrounds a free end of the disposable needle and a retracted position in which the protective shielding frame is retracted towards the first end of the housing relative to the extended position; wherein the protective shielding frame is arranged to provide manual access through an aperture in the protective shielding frame to the needle mounting hub when the protective shielding frame is in the extended position.

In a further aspect, a method is provided for of delivering liquid from a reusable sterilizable syringe, the method comprising: providing a reusable and sterilizable syringe comprising a housing and a protective shielding frame slidably engaged with the housing and movable between a retracted position and an extended position with respect to the housing, the housing comprising a needle mounting hub and the shielding frame comprising an aperture allowing manual access to the needle mounting hub when the shielding frame is in the extended position; mounting on the needle mounting hub a first disposable needle having a first needle tip; disposing within the housing a first disposable carpule containing a first liquid to place the first liquid in fluid communication with the needle; expressing the first liquid through the first disposable needle; moving the shielding frame to the extended position to cover the first needle tip after the expressing the first liquid; and manually removing the first disposable needle from the needle mounting hub through the aperture while the shielding frame is in the extended position. The method may further comprise sterilizing the syringe before the mounting the first disposable needle. The method may also further comprise: after the manually removing the first disposable needle from the needle mounting hub manually mounting on the needle hub through the aperture a second disposable needle while the shielding frame is in the extended position; and expressing the first liquid through the second disposable needle.

The method may further comprise after expressing the first liquid and before removing the first disposable needle: with the shielding frame in the extended position removing the first disposable carpule from the housing and disposing within the housing a second disposable carpule containing a second liquid to place the second liquid in fluid communication with the needle; and expressing the second liquid through the first disposable needle.

The mounting the first disposable needle may comprise mounting the first disposable needle manually via the aperture. The mounting the first disposable needle may comprise: providing the first disposable needle protected by a needle sheath; mounting the first disposable needle on the needle mounting hub; and disengaging the needle sheath from the first disposable needle by accessing the needle sheath through the aperture with the protective shielding frame in the extended position. The mounting the first disposable needle may comprise mounting the first disposable needle manually via the aperture.

The method may further comprise visually inspecting the carpule for aspirant through an aperture in the protective shielding frame when the protective shielding frame is in the retracted position. The inspecting may comprise directly visually inspecting the carpule.

In one embodiment, a conventional self-aspirating sterilizable dental anesthetic syringe is described, consisting of a housing that accommodates a carpule with a needle mounting hub on the top end and a sliding plunger at the lower most end of the housing. A harpoon type aspirating syringe body is another acceptable embodiment. The syringe further comprises a protective sliding mechanism, consisting of an open frame bearing two protective cylindrical collars, one at the furthermost end of each of the frame and one at a more proximal position. The positions of these protective collars correspond to the length of a commonly termed 'long' (1⅞ inches measured from the base of the needle mounting hub, 47.6 mm or known as 35 mm in Europe [as only referring to the length of the needle portion]) needle and 'short' (1½ inches measured from the base of the needle mounting hub, 38.1 mm or known in Europe as 25 mm) dental anesthetic needle. On the frame is a holding mechanism, which may be a temporary or transitory holding mechanism located on the proximal end. In some embodiments the holding mechanism may be a locking mechanism. A similar holding mechanism may be located on the distal end of the syringe housing. In that way, the protective collar cannot accidentally be dislodged from the safety position which covers an exposed needle tip.

A sheathed disposable needle is fastened onto a needle mounting hub at the distal or second end of the housing. This may be done either with the protective sliding mechanism retracted to a first holding position or extended to a second holding position, as the tip of the needle is safely covered by the sheath at this time. The plunger is retracted and an anesthetic carpule is then loaded into the chamber of the housing. In order to deliver the anesthetic, the protective sliding mechanism is extended to the second holding position where the tip of the needle is protected by the protective cylindrical collar. The sheath covering the conventional needle is first removed and placed aside, and the protective sliding mechanism is then retracted. This exposes the tip of the needle, and the operator performs the injection. At the conclusion of the injection, the operator slides the protective shielding mechanism forward to the second holding position, with the protective collars covering the tip of either the long or short length needle. A second anesthetic carpule or needle of different thickness or length may be loaded at this time. This procedure may be repeated over the length of the treatment. At the conclusion of treatment, with the protective sliding mechanism in the extended position, the needle may be disposed of directly into a sharps container by keeping the protective sliding mechanism forward, turning the syringe upside down, directing the needle end into the sharps container and unscrewing the needle at the needle mounting hub, thus allowing the needle to drop directly into the sharps container. The entire syringe apparatus may be sterilized and reused.

Embodiments of the invention will now be described in conjunction with the accompanying drawings in which:

BRIEF DESCRIPTION OF THE DRAWINGS

The foregoing and other features and advantages, either alone or in combinations of two or more, and the manner of attaining them, will become apparent from the following detailed description of embodiments, given by way of illustration and not limitation with reference to the accompanying drawings, in which.

DESCRIPTION OF EMBODIMENTS OF THE PRESENT INVENTION

The embodiments disclosed below are not intended to be exhaustive or limit the invention to the precise form disclosed in the following detailed description. Rather, the embodiments are chosen and described so that others skilled in the art may utilize its teachings.

Figure 1A:
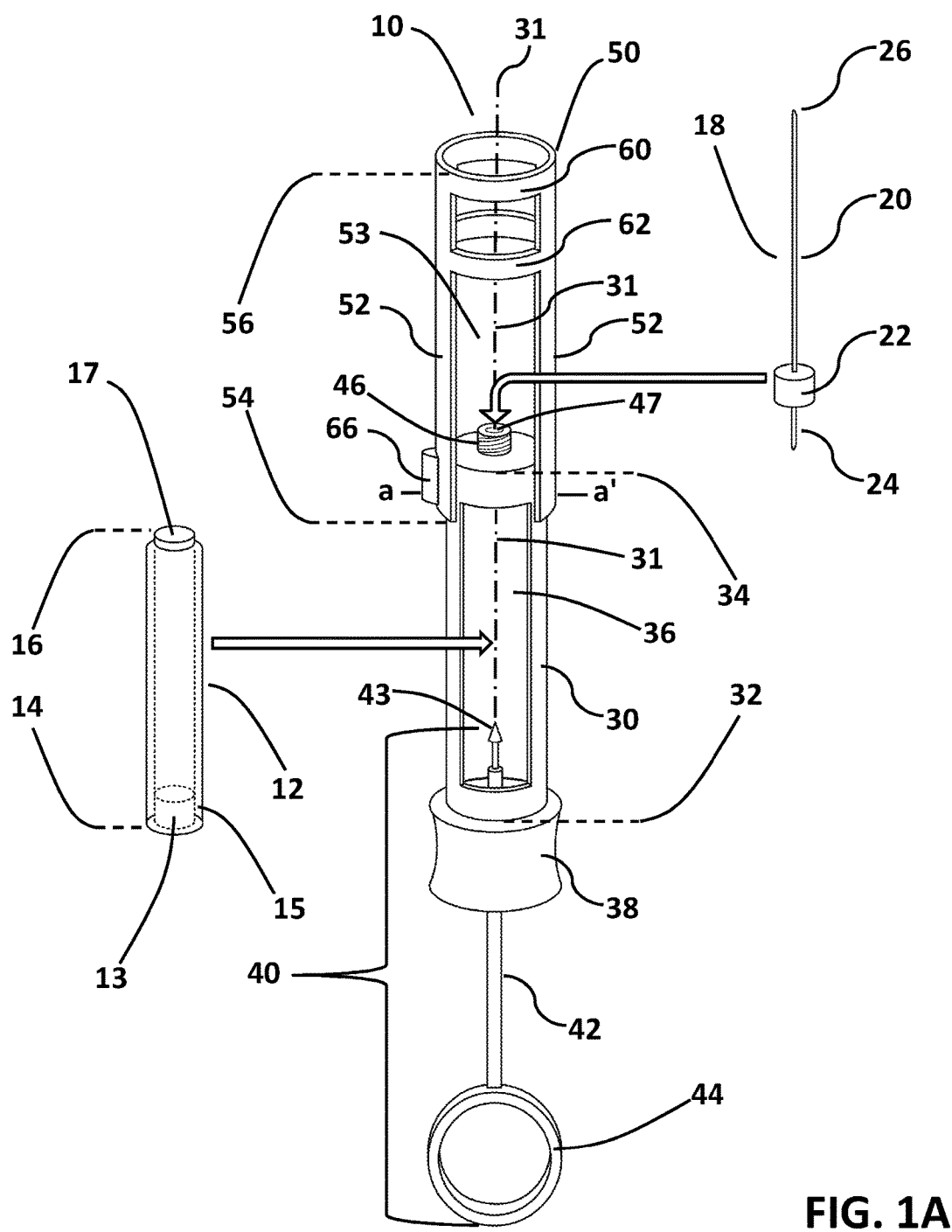
FIG. 1A is a perspective view of a syringe assembly of the present invention with a protective shielding frame shown in an extended position.

Referring to the accompanying figures, there is illustrated in FIG. 1A a reusable and sterilizable syringe assembly generally indicated by reference numeral 10. Assembly 10 is particularly suited for use with carpule 12 and disposable needle 18.

Carpule 12 is generally in the form of a disposable ampoule cartridge containing liquid medication to be delivered to the patient using syringe 10. Carpule 12 includes elongate tube 15 extending between first end 14 and second end 16. Second end 16 has sealed cap 17 which is puncturable. Plug 13 is mounted at first end 14 to define a sealed chamber between cap 17 and plug 13. The liquid medication is contained within the sealed chamber. In use, plug 13 is longitudinally slidable within tube 15 to dispense the medication through punctured cap 17.

Disposable needle 18 for use with syringe assembly 10 generally includes elongate primary needle portion 20 for injection of the liquid medication into a patient. Primary needle portion 20 has needle tip 26 for engaging the patient. Primary needle portion 20 is mounted on base 22 in the form of an internally threaded cap to permit threaded securement of needle 18 to housing 30 as described in further detail below and to extend along longitudinal 31 axis of housing 30 when mounted. Disposable needle 18 is commercially supplied with a protective sheath (not shown) for primary needle portion 20. The sheath ensures primary needle portion 20 is suitably sterilized when disposable needle 18 is mounted to housing 30.

Disposable needle 18 further includes inner needle portion 24 mounted internally within base 22 to extend axially inward opposite primary needle portion 20 for piercing sealed cap 17 of carpule 12 in use. The hollow interiors of primary needle portion 20 and inner needle portion 24 are in communication with each other to allow passage of the liquid medication from inner needle portion 24 through primary needle portion 20.

Syringe assembly 10 includes syringe housing 30 comprising a rigid tubular structure extending in a longitudinal direction about longitudinal axis 31 between first end 32 and opposing second end 34. The hollow interior of tubular syringe housing 30 defines a receptacle for receiving one of carpules 12 therein. Access opening 36 is provided in a side of the housing and is suitably sized for insertion and removal of carpule 12 therein. In the embodiment shown in FIG. 1, access opening 36 is in the form of an elongate slot. In the present specification, we refer to the side of syringe housing 30 containing opening 36 as the "front side" of syringe housing 30.

Finger grip 38 is provided on housing 30 at first end 32 of housing 30 to allow a user to establish a grip on syringe assembly 10. FIG. 1A shows one implementation of finger grip 38. Other implementations of finger grips may be, without limitation, in the form of two protrusions which extend laterally outward from opposing sides of front opening 36 at first end 32 of housing 30.

Plunger 40 is slidably mounted relative to first end 32 of housing 30. More particularly, plunger 40 includes elongate shaft 42 which is slidably mounted through a corresponding opening in an end wall at first proximal end 32 of housing 30 in order to move along longitudinal axis 31 of housing 30. Eyelet 44 at an outer end of shaft 42 defines a finger grip to control the longitudinal sliding of plunger 40 relative to housing 30. An inner end of shaft 42 of plunger 40 is adapted for engaging plug 13 of carpule 12. In some embodiments, as shown in FIG. 1A, the adaptation for shaft 42 to engage with plug 13 may be harpoon 43. In this manner, plunger 40 may be operated from an extended position in which it projects outward beyond first end 32 of housing 30 permitting insertion of carpule 12 into housing 30 to a retracted position in which elongate shaft 42 of plunger 40 is retracted into housing 30 so as to displace plug 13 of carpule 12 from first end 14 of carpule 12 towards second end 16 of carpule 12 to dispense thereby the medication from carpule 12 through needle 18 for delivery to the patient. In FIG. 1A, plunger 40 is shown in a partially retracted position so that harpoon 43 is visible through access opening 36.

Housing 30 further includes needle mounting hub 46 at second end 34 of housing 30. Needle mounting hub 46 is externally threaded for permitting base 22 of disposable needle 18 to be threaded onto needle mounting hub 46 in a mounted position. Needle mounting hub 46 includes through opening 47 to permit inner portion 24 of needle 18 to be received therethrough into puncturing engagement with sealed cap 17 of carpule 12.

Syringe assembly 10 further comprises protective shielding frame 50 slidingly engaged with syringe housing 30. Different embodiments may be employed for shielding frame 50, all embodiments having in common three aspects. The first common aspect is an ability to be extended along longitudinal axis 31 of housing 30 in order to cover needle tip 26 of needle 18 when needle 18 is mounted on needle mounting hub 46, and to directly observe carpule 12. The second common aspect is the ability to be retracted to expose substantially the entire working length of needle 18 when needle 18 is mounted on needle mounting hub 46. The third common aspect is the facility to grant mechanical access for the user to needle mounting hub 46 when shielding frame 50 is extended to cover needle tip 26 of needle 18. More particularly, this third aspect of all embodiments allows mechanical access to base 22 of needle 18 when shielding frame 50 is extended to cover needle tip 26 of needle 18. The phrase "substantially the entire working length of needle" is used in this specification to describe a length of needle 18, as measured from needle tip 26, as may be required to address any use of syringe assembly 10 in administering liquid medication to the patient.

One particular embodiment of shielding frame 50 is shown in FIG. 1A and will now be described at the hand of that figure. To accommodate the particular embodiment of shielding frame 50 shown in FIG. 1A, syringe housing 30 further includes two tracks 48 mounted at laterally opposing sides of the front opening to extend longitudinally substantially the full length of syringe housing 30 at diametrically opposed locations on syringe housing 30. Tracks 48 are obscured in FIG. 1A, and are therefore shown in FIG. 2, which is a cross-sectional diagram of syringe assembly 10 of FIG. 1A. The particular cross-section is taken perpendicular to longitudinal axis 31 between two opposing points a and a' on the external surface of protective shielding frame 50 in FIG. 1A.

Each track 48 comprises a groove recessed relative to the outer surface of syringe housing 30. The groove permits mounting of protective shielding frame 50 onto syringe housing 30 such that protective shielding frame 50 is longitudinally slidable between the extended and retracted positions described above. In FIG. 1A, protective shielding frame 50 is shown in the extended position. In the retracted position, protective shielding frame 50 is nearest to first end 32 of housing 30 so as to overlap housing 30 between first end 32 and second end 34 thereof along a substantial portion of protective shielding frame 50. In other embodiments, protective shielding frame 50, when retracted, may overlap housing 30 between first end 32 and second end 34 thereof along substantially the entire length of protective shielding frame 50. In the extended position, the protective shielding frame is positioned at its farthest location from first end 32 of housing 30 such that a substantial portion of protective shielding frame 50 protrudes longitudinally beyond second end 34 of syringe housing 30. In some embodiments, a majority of protective shielding frame 50, when frame 50 is in the extended position, protrudes longitudinally beyond second end 34 of syringe housing 30.

Figure 2:
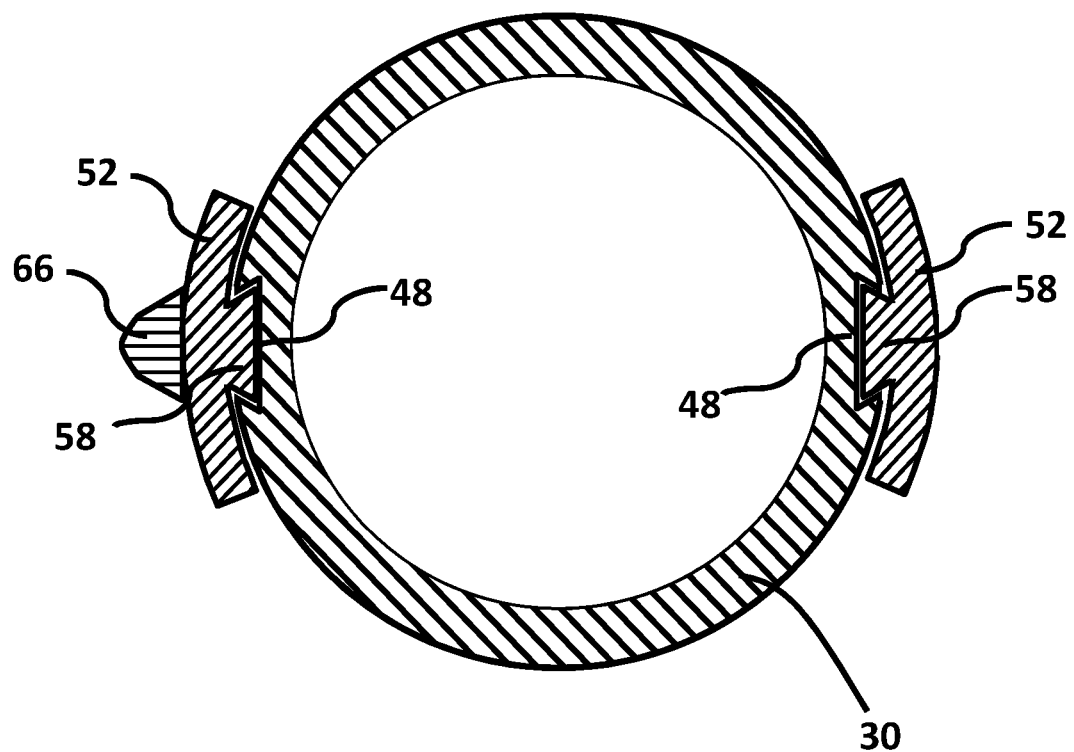
FIG. 2 is a cross-sectional view along the line a-a' of FIG. 1A or 1B.

Protective shielding frame 50 comprises two longitudinal frame members 52 spanning the full length of the protective shielding frame from first end 54 to second end 56 thereof. Each longitudinal frame member 52 is aligned with a respective one of tracks 48 in syringe housing 30 such that longitudinal frame members 52 are generally parallel to one another at diametrically opposed sides of syringe housing 30. As shown in FIG. 2, each longitudinal frame member 52 supports respective track follower 58 at a first end of longitudinal frame member 52 which protrudes generally radially inward for mating in sliding connection with a groove of respective track 48. In the embodiment shown in FIG. 2, followers 58 may have a dovetail shape which mates with a corresponding profile of the grooves such that followers 58 are retained within the grooves of tracks 48 and restricted to longitudinal relative sliding movement only. Each frame member 52 has an inner surface which is generally concave about a longitudinal axis of syringe housing 30.

Protective shielding frame 50 further may include first collar 60 and second collar 62 which are mounted concentrically with the central longitudinal axis of primary needle 20 and housing 30 and disposable needle 18 supported thereon. First collar 60 is mounted between longitudinal frame members 52 at second end 56 of frame 50 with the length of frame 50 being arranged such that, when used with disposable needle 18 having a first prescribed length, first collar 60 fully surrounds needle tip 26 of primary needle 20 and extends slightly longitudinally beyond needle tip 26 of primary needle 20 in the extended position of protective shielding frame 50.

Second collar 62 is mounted between longitudinal frame members 52 at a location spaced longitudinally inward relative to first collar 60. The position of second collar 62 corresponds to locating second collar 62 to fully surround and extend longitudinally outward beyond the free end of a primary needle of a second disposable needle having a second prescribed length when the protective shielding frame 50 is extended. For the sake of clarity, the second disposable needle is not shown in FIG. 1A. When treating a particular patient, often times multiple areas of the mouth need to be anesthetized. This is frequently done using multiple needles of differing lengths, diameters, and sharpness. The present invention allows for the exchange of needles as well as the safe disposal of contaminated needles directly through protective shielding frame 50. In some embodiments shielding frame 50 may optionally be made in different lengths to accommodate and/or match different lengths of needle 18, in other embodiments shielding frame 50 may be fashioned to be as long as the longest of possible needle 18.

In the retracted position of protective shielding frame 50, the longitudinal space between collar 62 and first end 54 of shielding frame 50 as measured along longitudinal axis 31 of housing 30, defines a shielding frame opening 53 which is aligned with the cap end of carpule 12 such that the portion of carpule 12 adjacent cap end 16 thereof may be visually inspected directly through the opening when shielding frame 50 is retracted. In this manner, direct visual inspection of aspirant is readily permitted. This is to be contrasted with some prior art systems in which the inspection of aspirant is done through a transparent window that may offer a less clear view of the aspirant. In the present specification, the phrases "directly visually inspecting" and "visually inspecting directly" are used to describe the straight line viewing of an object without any material other than the ambient air being between the observer and the object or using any reflection or refraction to view the object.

Figure 1B:
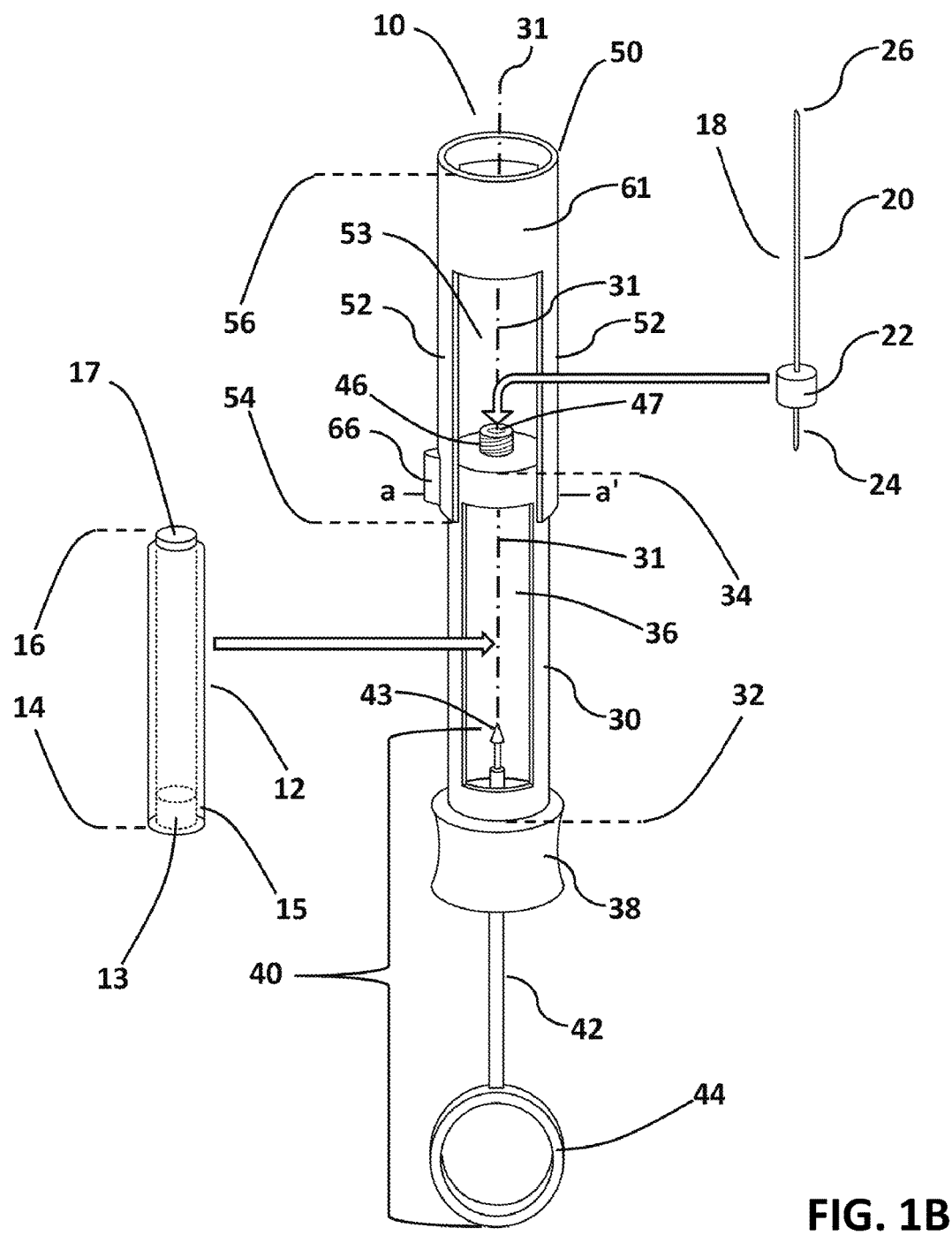
FIG. 1B is a perspective view of another embodiment of a syringe assembly of the present invention with a protective shielding frame shown in an extended position.

In another embodiment, shown in FIG. 1B, first and second collars 60 and 62 of FIG. 1A are not separated by a space or opening but form a continuous single collar 61 covering a range of lengths of primary needle. In all other respects FIG. 1B is identical to FIG. 1A. In this embodiment, carpule 12 may also be directly visually inspected through the aperture formed by the combination of shielding frame opening 53 and access opening 36 by sliding protective shielding frame 50 to its retracted position.

First end 54 of protective shielding frame 50 remains fully open at respective front and back sides to provide a further unobstructed view of the remainder of carpule 12 to also assist in viewing any aspirant within carpule 12 with protective shielding frame 50 in the retracted position. The openness of the front and rear sides of protective shielding frame 50 also allows for removal and replacement of a spent carpule with a new one while protective shielding frame 50 is kept in place because access opening 36 remains fully unobstructed by protective shielding frame 50 in the extended position and remains mostly unobstructed by protective shielding frame 50 in the retracted position.

The open front and rear sides of protective shielding frame 50 between two longitudinal frame members 52 also provides an aperture through which unobstructed access to base 22 of disposable needle 18 mounted on housing 30 even when protective shielding frame 50 remains in the extended position. In this manner, subsequent to use of needle 18 for delivering medication to a patient, protective shielding frame 50 may be extended to prevent inadvertent contact with needle 18 even as needle 18 is to be discarded by unthreading base 22 from needle mounting hub 46 of housing 30.

Protective shielding frame 50 may be retained in either one of the extended or retracted positions by a suitable holding mechanism. Suitable holding mechanisms include, without limitation, detents at the extended and retracted positions to ensure positive identification of positions when the detents are engaged. Many other suitable holding mechanisms are known in the art and will not further be dwelt upon in this specification. In FIG. 1 and FIG. 2 button 66 serves as a schematic representation of a generic holding mechanism. In this way, protective collar(s) 60, 61, 62 may not accidentally be dislodged from the safety position to expose needle tip 26 of needle 18. While, in some embodiments, the holding mechanism may be a locking mechanism, the mechanism may in other embodiments be a transitory or temporary holding mechanism.

Syringe assembly 10 may be made in its entirety from one or more dimensionally stable sterilizable medical grade materials, including without limitation, medical grade stainless steel and chrome plated brass. In the present specification the term "sterilizable" is used to describe materials that retain their chemical, structural and dimensional properties during sterilization to standards accepted in the medical and dental professions. Suitable sterilization processes include those described by the Centre for Disease Control in "Guideline for Disinfection and Sterilization in Healthcare Facilities", 2008 by Rutala, Weber, and the Healthcare Infection Control Practices Advisory Committee, and those described by the American Dental Association in the Journal of the American Dental Association, June 2001 Volume 132, Issue 6, Page 785.

The sterilization processes described in the above publications include sterilization by steam autoclave between 250° F. and 273° F., oven-type dry heat sterilization at 320° F. for 1 to 2 hours, rapid heat transfer-type dry heat sterilization at 375° F. for 6 to 20 minutes, and unsaturated chemical vapor sterilization in unsaturated formaldehyde or alcohol vapor at 273° F. for 20 minutes. Polymers employed in commercial disposable syringes generally do not retain their chemical, structural and dimensional properties under the action of such processes. Materials that do retain their chemical, structural and dimensional properties under the action of such processes include, but are not limited to, medical grade stainless steel, chrome plated brass, and autoclavable polymers. In this specification, the term "autoclavable" is used to describe materials that retain their chemical, structural and dimensional properties when sterilized in a steam autoclave at temperatures of at least 250° F. More particularly preferred are materials that retain their chemical, structural and dimensional properties when sterilized in a steam autoclave at temperatures of 273° F.

The shaft of needle 18 is not of a safety concern, as it is smooth and does not contribute to needle stick injury. It is at needle tip 26, being at the sharp working end of needle 18, where accidental injuries may and do occur. Thus, having protective collar 60, 61, 62 proximate second end 56 of protective shielding frame 50 prevents sharp needle stick injuries. All embodiments described in the present specification allow for a substantial shielding frame opening 53 at the base of protective shielding frame 50. This opening 53 permits direct finger access to needle base 22 and needle mounting hub 46, while shielding frame 50 protects sharp needle tip 26 by means of collar 60, 61, 62. This direct finger access enables the replacement of one disposable needle 18 for another during a single patient care visit. The replacement needle may be of a different length, corresponding to one of collars 60, 61, 62, or may be of a different diameter. One or more carpules 12 may be employed with the different needles. At the completion of patient care, needle 18 may be disposed of. Syringe apparatus 10 as per FIG. 1 may then be sterilized and reused on another patient. This is to be contrasted with prior art systems in which the needle is substantially covered by a slidable shield and in which it is not possible to retain and sterilize the entire syringe system.

Figure 3:
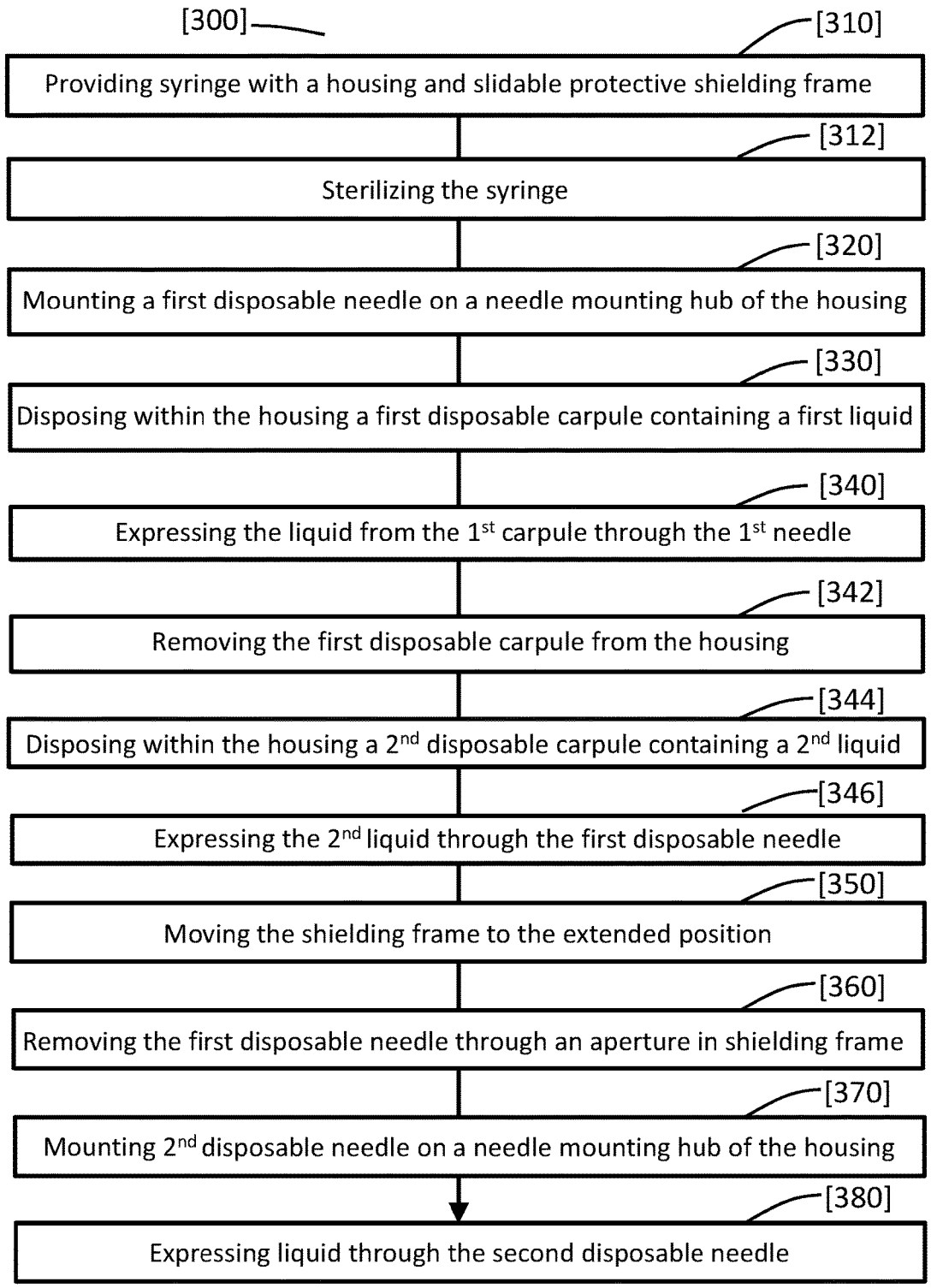
FIG. 3 shows a flow chart describing a method for attaching a needle to the syringe assembly of the present invention Corresponding reference characters indicate corresponding parts throughout the several views. Although the drawings represent embodiments of the present invention, the drawings are not necessarily to scale and certain features may be exaggerated in order to better illustrate and explain the full scope of the present invention. The flow charts and screen shots are also representative in nature, and actual embodiments of the invention may include further features or steps not shown in the drawings. The exemplification set out herein illustrates an embodiment of the invention, in one form, and such exemplifications are not to be construed as limiting the scope of the invention in any manner.

In a further aspect, described at the hand of the flow chart in FIG. 3, method [300] is provided for of delivering liquid from reusable sterilizable syringe 10, the method comprising: providing [310] a reusable and sterilizable syringe 10 comprising housing 30 and protective shielding frame 50 slidably engaged with housing 30 and movable between a retracted position and an extended position with respect to housing 30, housing 30 comprising needle mounting hub 46 and shielding frame 50 comprising aperture 53 allowing manual access to needle mounting hub 46 when shielding frame 50 is in the extended position; mounting [320] on needle mounting hub 46 a first disposable needle 18 having a first needle tip 26; disposing [330] within the housing a first disposable carpule 12 containing a first liquid to place the first liquid in fluid communication with the needle 18; [340] expressing the first liquid through the first disposable needle; [350] moving shielding frame 50 to the extended position to cover the first needle tip 26 after the expressing [340] the first liquid; and manually removing [360] first disposable needle 18 from needle mounting hub 46 through aperture 53 while shielding frame 50 is in the extended position.

The method may further comprise sterilizing [312] syringe 10 before mounting [320] first disposable needle 18. The method may also further comprise: after the manually removing [360] first disposable needle 18 from needle mounting hub 46 manually mounting [370] on needle hub 46 through aperture 53 a second disposable needle while shielding frame 50 is in the extended position; and expressing [380] liquid through the second disposable needle. If the first carpule 12 is disposed in housing 30 at the time of step [380], then first liquid is expressed in step [380]. If the second carpule is disposed in housing 30 at the time of step [380], then second liquid is expressed in step [380]. Steps [342] to [346]; and steps [370] to [380] are independently optional.

The method [300] may further optionally comprise after expressing [340] the first liquid and before removing [360] the first disposable needle 18: with shielding frame 50 in the extended position removing [342] first disposable carpule 12 from housing 30 and disposing [344] within housing 30 a second disposable carpule containing a second liquid to place the second liquid in fluid communication with the first disposable needle 18; and expressing [346] the second liquid through first disposable needle 18.

The mounting [320] of first disposable needle 18 may comprise mounting first disposable needle 18 manually via aperture 53. Mounting first disposable needle [320] may more specifically comprise: providing the first disposable needle 18 protected by a needle sheath (not shown in FIG. 1); mounting first disposable needle 18 on needle mounting hub 46; and disengaging the needle sheath from first disposable needle 18 by accessing the needle sheath through aperture 53 with protective shielding frame 50 in the extended position. The mounting the first disposable needle 18 may comprise mounting first disposable needle 18 manually via aperture 53.

The method [300] may further comprise visually inspecting the carpule for aspirant through aperture 53 in protective shielding frame 50 when protective shielding frame 50 is in the retracted position. The inspecting may comprise directly visually inspecting the carpule.

Since various modifications may be made in the invention as herein above described, it is intended that all matter contained in the accompanying specification shall be interpreted as illustrative only and not in a limiting sense. While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A reusable syringe assembly for use with a disposable carpule containing a liquid and a disposable needle with a tip having a sharp free end, the assembly comprising: a syringe housing extending longitudinally between a first housing end and a second housing end, the housing having an access opening suitably sized to permit the carpule to be inserted into and removed from the housing therethrough, the housing having a needle mounting hub adapted to receive and replace thereon the disposable needle tip and defining a receptacle arranged to receive therein the carpule such that the carpule is in fluid communication with the disposable needle tip; and a protective shielding frame supported on the housing for longitudinal sliding between a first extended position in which the protective shielding frame protrudes longitudinally beyond the second housing end to surround the sharp free end of the disposable needle tip and a second retracted position in which the protective shielding frame is retracted towards the first housing end relative to the extended position; wherein the protective shielding frame is structured and arranged to provide access through an aperture in the protective shielding frame for manual attachment to and removal from the second housing end of the disposable needle tip when the protective shielding frame is in the extended position, and to provide access for manual insertion and removal of a carpule through the access opening in the retracted position.

2. The assembly according to claim 1 wherein the protective shielding frame is arranged to render the disposable carpule visible through the protective shielding frame when the protective shielding frame is in the retracted position.

3. The assembly according to claim 2, wherein the protective shielding frame is arranged to render the disposable carpule visible through the protective shielding frame when the protective shielding frame is in the retracted position.

4. The assembly according to claim 1, wherein the housing includes along one side thereof an access opening suitably sized to permit the carpule to be inserted into and removed from the housing therethrough, the protective shielding frame being supported on the housing such that the access opening is unobstructed by the protective shielding frame when the protective shielding frame is in at least the extended position of the protective shielding frame.

5. The assembly according to claim 1, wherein the protective shielding frame comprises at least one longitudinal frame member and at least one collar portion fixed to the longitudinal frame member so as to surround the disposable needle tip.

6. The assembly according to claim 5, wherein said at least one collar portion comprises two collar portions at longitudinally spaced positions.

7. The assembly according to claim 1, further comprising a plunger arranged to operatively engage the carpule and supported for longitudinal sliding movement relative to the first end of the housing.

8. The assembly according to claim 7, wherein the plunger includes a finger grip portion and an eyelet.

9. The assembly according to claim 1, wherein the syringe assembly is made of material that is reusable and does not deform when subjected to sterilizing conditions.

10. The assembly according to claim 1, wherein the syringe assembly is reusable and made from one or more dimensionally stable sterilizable medical grade materials.

11. The assembly according to claim 1, wherein the syringe assembly is reusable and made from at least one of medical grade stainless steel and chrome plated brass.

12. The assembly according to claim 1, wherein the syringe assembly is reusable and made from at least one autoclavable polymer.

13. A reusable syringe assembly for use with a disposable needle having a tip, and a disposable carpule, the assembly comprising:
a housing extending longitudinally between a first end and a second end adapted to support the removal and replacement of the disposable needle tip thereon and defining a receptacle therein, the housing having an access opening suitably sized to permit the carpule to be inserted into and removed from the receptacle therethrough, the receptacle arranged to receive therein the carpule such that the carpule is cooperative with the disposable needle tip;
a plunger supported for sliding movement relative to the first end of the housing so as to be arranged to operatively engage the carpule; and
a protective shielding frame supported on the housing for longitudinal sliding between an extended position in which the protective shielding frame protrudes longitudinally beyond the second end of the housing and surrounds a free end of the disposable needle tip and a retracted position in which the protective shielding frame is retracted towards the first end of the housing relative to the extended position;
wherein the protective shielding frame is arranged to provide access through the protective shielding frame for manual attachment to and removal from the second housing end of the disposable needle tip when the protective shielding frame is in the extended position.

14. The assembly according to claim 13 wherein the protective shielding frame is arranged to render the disposable carpule visible through the protective shielding frame when the protective shielding frame is in the retracted position.

15. The assembly according to claim 14, wherein the protective shielding frame is arranged to render the disposable carpule visible through the protective shielding frame when the protective shielding frame is in the retracted position.

16. The assembly according to claim 13, wherein the housing includes along one side thereof an access opening suitably sized to permit the carpule to be inserted into and removed from the housing therethrough, the protective shielding frame being supported on the housing such that the access opening is unobstructed by the protective shielding frame when the protective shielding frame is in at least the extended position of the protective shielding frame.

17. The assembly according to claim 13, wherein the protective shielding frame comprises at least one longitudinal frame member and at least one collar portion fixed to the longitudinal frame member so as to surround a tip of the disposable needle tip.

18. The assembly according to claim 17, wherein said at least one collar portion comprises two collar portions at longitudinally spaced positions.

19. The assembly according to claim 13, wherein the plunger includes a finger grip portion and an eyelet.

20. The assembly according to claim 13, wherein the syringe assembly is reusable and made of material that does not deform when subjected to sterilizing conditions.

21. The assembly according to claim 13, wherein the syringe assembly is reusable and made from one or more dimensionally stable sterilizable medical grade materials.

22. The assembly according to claim 13, wherein the syringe assembly is reusable and made from at least one of medical grade stainless steel and chrome plated brass.

23. The assembly according to claim 13, wherein the syringe assembly is reusable and made from at least one autoclavable polymer.

24. A method of delivering liquid from a sterilizable syringe that is reusable, the method comprising:
providing a reusable and sterilizable syringe comprising a housing and a protective shielding frame movably engaged with the housing;
providing a first disposable needle tip having a first sharp free end;

first moving the shielding frame to an extended position relative to the housing;
first engaging with the housing a first disposable carpule containing a first liquid;
first manually attaching to the housing the first disposable needle tip in fluid communication with an interior of the first carpule while the first sharp free end is substantially covered by the shielding frame in the extended position; and
first expressing the first liquid from the first disposable carpule through the first disposable needle tip, further comprising:
after the first expressing step third moving the shielding frame to the extended position relative to the housing;
second engaging with the housing a second disposable carpule containing one of the first and a second liquid;
third replacing the first disposable needle tip with a second disposable needle tip having a second sharp free end;
after the third moving the shielding frame to the extended position manually second attaching to the housing the second disposable needle tip in fluid communication with an interior of the second carpule while the second sharp free end is substantially covered by the shielding frame in the extended position; and
second expressing the one of the first and the second liquid from the second disposable carpule through the second disposable needle tip.

25. The method of claim 24, further comprising exposing the first sharp free end by second moving the shielding frame to a retracted position after the first manually attaching step and before the first expressing step.

26. The method of claim 24, further comprising exposing the second sharp free end by fourth moving the shielding frame to the retracted position after a second manually attaching step and before the second expressing step.

27. The method of claim 24, further comprising sterilizing the syringe after the first expressing step and before both of the second engaging with the housing a second disposable carpule and the manually second attaching to the housing the second disposable needle tip.

28. The method of claim 24, further comprising manually removing from the housing the first disposable needle tip after the third moving the shielding frame to the extended position relative to the housing.

29. The method of claim 24, further comprising sterilizing the syringe before both of the first engaging with the housing the first disposable carpule and the manually first attaching to the housing the first disposable needle tip.

30. A method of delivering liquid from a sterilizable syringe that is reusable, the method comprising:
providing a reusable and sterilizable syringe comprising a housing and a protective shielding frame movably engaged with the housing;
providing a first disposable needle tip having a first sharp free end;
first moving the shielding frame to an extended position relative to the housing;
first engaging with the housing a first disposable carpule containing a first liquid;
first manually attaching to the housing the first disposable needle tip in fluid communication with an interior of the first carpule while the first sharp free end is substantially covered by the shielding frame in the extended position; and
first expressing the first liquid from the first disposable carpule through the first disposable needle tip, further comprising after expressing the first liquid and before removing the first disposable needle:
with the shielding frame in the extended position removing the first disposable carpule from the housing and disposing within the housing a second disposable carpule containing a second liquid to place the second liquid in fluid communication with the needle; and
expressing the second liquid through the first disposable needle.

31. The method of claim 30, further comprising sterilizing the syringe before the mounting the first disposable needle.

32. A method of delivering liquid from a sterilizable syringe that is reusable, the method comprising:
providing a reusable and sterilizable syringe comprising a housing and a protective shielding frame movably engaged with the housing;
providing a first disposable needle tip having a first sharp free end;
first moving the shielding frame to an extended position relative to the housing;
first engaging with the housing a first disposable carpule containing a first liquid;
first manually attaching to the housing the first disposable needle tip in fluid communication with an interior of the first carpule while the first sharp free end is substantially covered by the shielding frame in the extended position; and
first expressing the first liquid from the first disposable carpule through the first disposable needle tip, wherein the first manually attaching step comprises:
providing the first disposable needle protected by a needle sheath;
mounting the first disposable needle on the needle mounting hub; and
disengaging the needle sheath from the first disposable needle by accessing the needle sheath through the aperture with the protective shielding frame in the extended position.

33. The method of claim 32, further comprising sterilizing the syringe before the mounting the first disposable needle.

34. A method of delivering liquid from a sterilizable syringe that is reusable, the method comprising:
providing a reusable and sterilizable syringe comprising a housing and a protective shielding frame movably engaged with the housing;
providing a first disposable needle tip having a first sharp free end;
first moving the shielding frame to an extended position relative to the housing;
first engaging with the housing a first disposable carpule containing a first liquid;
first manually attaching to the housing the first disposable needle tip in fluid communication with an interior of the first carpule while the first sharp free end is substantially covered by the shielding frame in the extended position; and
first expressing the first liquid from the first disposable carpule through the first disposable needle tip, wherein the mounting the first disposable needle comprises mounting the first disposable needle manually via the aperture.

35. The method of claim 34, further comprising sterilizing the syringe before the mounting the first disposable needle.

36. A method of delivering liquid from a sterilizable syringe that is reusable, the method comprising:

providing a reusable and sterilizable syringe comprising a housing and a protective shielding frame movably engaged with the housing;

providing a first disposable needle tip having a first sharp free end;

first moving the shielding frame to an extended position relative to the housing;

first engaging with the housing a first disposable carpule containing a first liquid;

first manually attaching to the housing the first disposable needle tip in fluid communication with an interior of the first carpule while the first sharp free end is substantially covered by the shielding frame in the extended position; and first expressing the first liquid from the first disposable carpule through the first disposable needle tip, further comprising:

after the manually removing the first disposable needle from the needle mounting hub manually mounting on the needle hub through the aperture a second disposable needle while the shielding frame is in the extended position; and expressing the first liquid through the second disposable needle.

37. The method of claim 36, further comprising visually inspecting the carpule for aspirant through the aperture in the protective shielding frame when the protective shielding frame is in the retracted position.

38. The method of claim 36, wherein the visually inspecting comprises directly visually inspecting.

39. A method of operating syringe assembly for use with a disposable carpule containing a liquid and a disposable needle having a needle tip, the assembly having a syringe housing extending longitudinally between a first housing end and a second housing end, the housing having an access opening suitably sized to permit the carpule to be inserted into and removed from the housing therethrough, the housing having a needle mounting hub adapted to receive and replace thereon the disposable needle and defining a receptacle arranged to receive therein the carpule such that the carpule is in fluid communication with the disposable needle tip; and a protective shielding frame supported on the housing for longitudinal sliding between a first extended position in which the protective shielding frame protrudes longitudinally beyond the second housing end to surround the needle tip of the disposable needle tip and a second retracted position in which the protective shielding frame is retracted towards the first housing end relative to the extended position, the method comprising:

sliding the protective shielding frame into the extended position subsequent to use of the carpule; and removing the disposable needle tip from the second end of the housing while the protective shielding frame remains in the extended position.

* * * * *